United States Patent [19] [11] 4,244,883
Youngdale [45] Jan. 13, 1981

[54] 2A,2B-DIHOMO-15-ALKYL-PGF$_{2\beta}$ COMPOUNDS

[75] Inventor: Gilbert A. Youngdale, Portage, Mich.

[73] Assignee: The Upjohn Company, Kalamazoo, Mich.

[21] Appl. No.: 74,696

[22] Filed: Sep. 12, 1979

Related U.S. Application Data

[60] Continuation-in-part of Ser. No. 3,153, Jan. 15, 1979, abandoned, which is a continuation of Ser. No. 884,430, Mar. 8, 1978, abandoned, which is a division of Ser. No. 663,362, Mar. 3, 1976, Pat. No. 4,082,783, which is a division of Ser. No. 551,220, Oct. 10, 1974, Pat. No. 3,974,195.

[51] Int. Cl.³ ................................................ C07C 177/00
[52] U.S. Cl. ........................... 260/410.9 R; 260/404; 260/405.5; 260/413
[58] Field of Search ............ 260/404, 404.5, 410.9 R, 260/413

[56] References Cited

U.S. PATENT DOCUMENTS

| | | | |
|---|---|---|---|
| 3,728,382 | 4/1973 | Bundy | 562/503 |
| 3,816,393 | 6/1974 | Hayashi | 260/209 |
| 3,852,382 | 12/1974 | Beal | 260/413 |

*Primary Examiner*—Robert Gerstl
*Attorney, Agent, or Firm*—Robert A. Armitage

[57] ABSTRACT

The present invention relates to novel cytoprotective 2a,2b-dihomo-15-alkyl-PGF$_{2\beta}$ compounds.

7 Claims, No Drawings

2A,2B-DIHOMO-15-ALKYL-PGF$_{2\beta}$ COMPOUNDS

CROSS REFERENCE TO RELATED APPLICATIONS

The present application is a continuation-in-part of U.S. Ser. No. 003,153, filed Jan. 15, 1979, now abandoned; which is a continuation of U.S. Ser. No. 884,430, filed Mar. 8, 1978, now abandoned; which is a divisional application of U.S. Ser. No. 663,362, filed Mar. 3, 1976, issued on Apr. 4, 1978 as U.S. Pat. No. 4,082,783; which is a divisional application of U.S. Ser. No. 551,220, filed Oct. 10, 1974, issued on Aug. 10, 1976 as U.S. Pat. No. 3,974,195.

BACKGROUND OF THE INVENTION

The present invention relates to novel pharmacological agents, particularly prostaglandin analogs. The present invention provides novel 2a,2b-dihomo-15-alkyl-PGF$_{2\alpha}$ compounds, a description of which, including their preparation and pharmacological uses, is incorporated here by reference from U.S. Pat. No. 3,974,195.

PRIOR ART 2a,2b-Dihomo-PGF compounds are known. See U.S. Pat. No. 3,852,316.

SUMMARY OF THE INVENTION

The present invention particularly provides: An optically active compound of the formula:

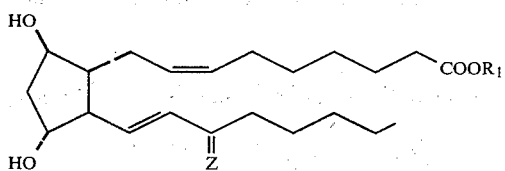

wherein
Z is $\alpha$-OH:$\beta$-CH$_3$, $\alpha$-CH$_3$:$\beta$-OH, $\alpha$-OH:$\beta$-CH$_2$CH$_3$, or $\alpha$-CH$_2$CH$_3$:$\beta$-OH; and
wherein R$_1$ is hydrogen, alkyl of one to 12 carbon atoms, inclusive,
—(p-Ph)—NH—CO—(p—Ph)—NH—CO—CH$_3$,
—(p-Ph)—NH—CO—(p—Ph),
—(p-Ph)—NH—CO—CH$_3$,
—(p-Ph)—NH—CO—NH$_3$,
—(p-Ph)—CH=N—NH—CO—NH$_2$,
—$\beta$—naphthyl, wherein p-Ph is para-substituted phenyl or p-phenylene, or pharmacologically acceptable salts thereof when R$_1$ is hydrogen.

With regard to the divalent substituent described above, i.e., Z, this divalent radical is defined as $\alpha$-R$_i$:$\beta$-R$_j$, where R$_i$ represents a substituent of the divalent moiety of the alpha configuration with respect to the cyclopentane ring and R$_j$ represents a substituent of the divalent moiety of the beta configuration with respect to the cyclopentane ring. Accordingly, when Z is defined as $\alpha$-OH:$\beta$-CH$_3$, the hydroxy of the Z moiety is in the alpha configuration, i.e. as in PGF$_{2\alpha}$, and the CH$_3$ substituent is in the beta configuration.

Particular embodiments of the present invention include:
2a,2b-Dihomo-15(S)-15-methyl-PGF$_{2\beta}$;
2a,2b-Dihomo-15(S)-15-methyl-PGF$_{2\beta}$, methyl ester;
2a,2b-Dihomo-15(R)-15-methyl-PGF$_{2\beta}$; and
2a,2b-Dihomo-15(R)-15-methyl-PGF$_{2\beta}$, methyl ester.

While the novel compounds of the instant invention exhibit pharmacolgocial effects characteristic of the prostaglandins, these compounds represent particularly improved gastrointestinal cytoprotective compounds as compared to the 2a,2b-dihomo-PGF compounds of the prior art.

The gastrointestinal cytoprotective property of the novel prostaglandin analogs herein is evidenced by the ability of these compounds to inhibit the formation of ulcers or other lesions in standard laboratory animals treated with gastrointestinally erosive agents. For a discussion of such laboratory tests, describing the prevention of these gastric lesions by pre-treatment with prostaglandins, see Robert, et al., "Gastric Cytoprotective Property of Prostaglandins", Gastroenterology 72:1121 (1977); and a discussion of such laboratory tests, describing the reduction in intestinal lesions by pre-treatment with prostaglandins, see Robert, et al., Gastroenterology 69:1045 (1974), wherein, inter alia, PGE$_2$ is demonstrated to be effective in reducing indomethacin-induced intestinal lesions in the rat.

By virtue of the gastrointestinal cytoprotective property of the novel prostaglandin analogs herein, these compounds are highly useful in the prevention and treatment of inflammatory diseases of the stomach, duodenum, and large and small intestine. For example, the novel prostaglandin analogs herein are employed as gastric cytoprotective agents in the prevention and treatment of gastric erosive diseases, such as gastric ulceration and erosive gastritis. Moreover, the novel prostaglandin analogs herein are useful as intestinal cytoprotective agents in the treatment of numerous intestinal inflammatory diseases, included in which are Crohn's disease, inflammatory bowel disease, infectious enteritis, sprue, and intestinal inflammatory diseases secondary to radiation exposure or allergen exposure. While the novel prostaglandin analogs herein are useful for the present gastrointestinal cytoprotective purposes in a wide variety of mammals, including valuable domestic animals, the principal use of the novel prostaglandin analogs herein is in man.

Accordingly, by this preferred embodiment of the gastric cytoprotective use, the novel prostaglandin analogs are used in man for the treatment and prevention of gastric ulcer, duodenal ulcer, gastritis and other gastric inflammatory conditions (e.g., secondary to radiation exposure), by the systemic administration of a dose of a novel prostaglandin analog effective to treat or prevent the development of the disease. In the prophylactic use of these gastric cytoprotective prostaglandins, patients are selected for treatment who exhibit a high susceptibility to the acquisition of a gastric inflammatory disease. Examples of such patients include those with a previous history of gastric or duodenal ulcer; those persons subjected to chronic or acute and stressful environmental conditions, whether of a physical or emotional origin; those manifesting chronic and excessive ethanol consumption (e.g., especially persons diagnosed as alcoholics); and those persons for whom an acute exposure to a cytodestructive dose of ionizing radiation is contemplated. In the latter case, the use of the novel prostaglandin analogs herein in patients receiving therapeutic doses of radiation, for example in the treatment of neoplastic diseases, is particularly contemplated.

When the novel prostaglandin analogs herein are employed as enteric cytoprotective agents, the prophylactic or therapeutic use is undertaken when the animal or patient is in a state of high susceptibility to the development of an intestinal inflammatory disease or the diagnosis of such a disease has been made. Examples of patients exhibiting a high susceptibility to the development of enteric inflammatory diseases include, for example, patients subject to cytodestructive doses of radiation, as indicated above.

With regard to the systemic administration of the novel compounds of the present invention, any convenient systemic route is employed, although oral administration is the highly preferred route. While the oral route is preferred, for patients where this route of administration is inconvenient or unacceptable, other routes such as via a nasogastric tube or via suppositories and enemas are likewise preferred. For a description of the various methods of formulation and routes of administration by which the novel prostaglandin analogs herein are employed, see U.S. Pat. No. 3,903,297.

The dosage regimen and duration of treatment for the novel prostaglandin analogs herein will depend upon a wide variety of factors, including the type, age, weight, sex, medication condition of the animal or patient being treated and the nature and severity of the gastric or enteric inflammatory disesase to be treated or prevented. For example, oral doses between 25 mg/kg/day and 0.5 µg/kg/day will ordinarily be gastrointestinally cytoprotective. Once a minimum effective dose for the particular novel prostaglandin analog herein is determined for a particular animal or patient, that animal or patient is thereafter advantageously provided with a daily dosage schedule which will provide a substantially uniform level of the novel cytoprotective analog throughout the day.

Moreover, treatment with the novel prostaglandin analog herein should be continued therapeutically until the gastrointestinal inflammatory disease has been successfully arrested, and thereafter a prophylactic regimen with the prostaglandin analog should be maintained until susceptibility to the recurrence of the disease is no longer high. Thus, in the case of an acute exposure to a noxious agent, treatment for several days to several weeks will ordinarily be sufficient. However, in cases where a patient, for example, has a history of multiple recurrences of gastric or duodenal ulcer, prophylactic treatment may be maintained indefinitely, based upon the continued tolerance to the drug.

DESCRIPTION OF THE PREFERRED EMBODIMENTS

Example 1 Cytoprotective effects of 2a,2b-dihomo-15-methyl-PGF$_{2\beta}$, methyl ester as compared to 2a,2b-dihomo-PGF$_{2\beta}$, methyl ester.

Female rats of 205-220 g are deprived of food during the morning. At 1500 hrs, water is removed and the animals are placed in individual cages which prevent them from consuming hair or feces. The following morning, the prostaglandin analogs are administered orally at a fixed dose of 2 mg/kg in 1 ml of water containing 5% ethanol and 1% emulphor. Emulphor EL-620 is used. Thirty minutes later, 1 ml of ethanol (80%) is given orally to induce gastric lesions. One hour after ethanol administration, the animals are sacrificed with carbon dioxide, their stomachs disected out and opened along the greater curvature. Visual examination with a binocular magnifier is undertaken to determine the presence of necrotic ulcerations. The average number of ulcers per stomach is recorded. The control group of rats receiving only vehicle (ethanol 5%, emulphor 1% in water) prior to the administration of 80% ethanol is employed. From the number of ulcerations in control group animals, a percent inhibition is determined which is the percent reduction in the number of gastric lesions in the treated group as compared to the control group.

The results, reported in Table A, indicate that 2a,2b-dihomo-15-methyl-PGF$_{2\beta}$, methyl ester, is virtually totally cytoprotective, while the prior art compound, 2a,2b-dihomo-PGF$_{2\beta}$, methyl ester, demonstrates only modest cytoprotective effects.

Example 2 Cytoprotective effects of 2a,2b-dihomo-15-epi-15-methyl-PGF$_{2\beta}$, methyl ester as compared to 2a,2b-dihomo-15-epi-PGF$_{2\beta}$, methyl ester.

Following the procedure of Example 1, 2a,2b-dihomo-15-epi-PGF$_{2\beta}$, methyl ester is compared for gastrointestinal cytoprotective activity with 2a,2b-dihomo-15-epi-15-methyl-PGF$_{2\beta}$, methyl ester. The results of this experiment, reported in Table A, indicate that 2a,2b-dihomo-15-epi-15-methyl-PGF$_{2\beta}$, methyl ester, is totally cytoprotective, while the prior art 2a,2b-dihomo-15-epi-PGF$_{2\beta}$, methyl ester, exhibits negligable cytoprotective effects.

TABLE A

| Compound | % Inhibition |
|---|---|
| 2a,2b-dihomo-PGF$_{2\beta}$, methyl ester | 32 |
| 2a,2b-dihomo-15-methyl-PGF$_{2\beta}$, methyl ester | 96 |
| 2a,2b-dihomo-15-epi-PGF$_{2\beta}$, methyl ester | 2 |
| 2a,2b-dihomo-15-epi-15-methyl-PGF$_{2\beta}$, methyl ester | 100 |

What is claimed is:
1. An optically active compound of the formula:

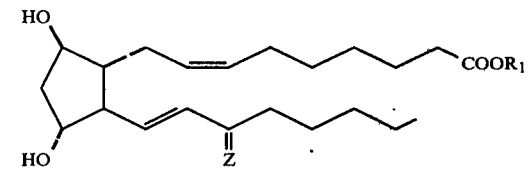

wherein
Z is $\alpha$-OH:$\beta$-CH$_3$, $\alpha$-CH$_3$:$\beta$-OH, $\alpha$-OH:$\beta$-CH$_2$CH$_3$, or $\alpha$-CH$_2$CH$_3$:$\beta$-OH; and
wherein R$_1$ is hydrogen, alkyl of one to 12 carbon atoms, inclusive,
—(p-Ph)—NH—CO—(p-Ph)—NH—CO—CH$_3$,
—(p-Ph)—NH—CO—(p-Ph),
—(p-Ph)—NH—CO—CH$_3$,
—(p-Ph)—NH—CO—NH$_3$,
—(p-Ph)—CH=N—NH—CO—NH$_2$,
-p-naphthyl, wherein p-Ph is para-substituted phenyl or p-phenylene, or pharmacologically acceptable salts thereof when R$_1$ is hydrogen.

2. A compound according to claim 1, wherein Z is $\alpha$-OH:$\beta$-CH$_3$.

3. 2a,2b-Dihomo-15(S)-15-methyl-PGF$_{2\beta}$, a compound according to claim 2, wherein R$_1$ is hydrogen.

4. 2a,2b-Dihomo-15(S)-15-methyl-PGF$_{2\beta}$, methyl ester, a compound according to claim 2, wherein R$_1$ is methyl.

5. A compound according to claim 1, wherein Z is $\beta$-OH:$\alpha$-CH$_3$.

6. 2a,2b-Dihomo-15(R)-15-methyl-PGF$_{2\beta}$, a compound according to claim 5, wherein R$_1$ is hydrogen.

7. 2a,2b-Dihomo-5(R)-15-methyl-PGF$_{2\beta}$, methyl ester, a compound according to claim 5, wherein R$_1$ is methyl.

* * * * *

UNITED STATES PATENT OFFICE
CERTIFICATE OF CORRECTION

Patent No. 4,244,883    Dated 13 January 1981

Inventor(s) Gilbert A. Youngdale

It is certified that error appears in the above-identified patent and that said Letters Patent are hereby corrected as shown below:

Column 1, line 21, "$PGF_{2\alpha}$ compounds" should read -- $PGF_{2\beta}$ compounds --.

Signed and Sealed this

Twenty-eighth Day of April 1981

[SEAL]

Attest:

RENE D. TEGTMEYER

Attesting Officer    Acting Commissioner of Patents and Trademarks